(12) United States Patent
Gharib et al.

(10) Patent No.: US 9,050,444 B2
(45) Date of Patent: Jun. 9, 2015

(54) DRUG DELIVERY AND SUBSTANCE TRANSFER FACILITATED BY NANO-ENHANCED DEVICE HAVING ALIGNED CARBON NANOTUBES PROTRUDING FROM DEVICE SURFACE

(71) Applicant: California Institute of Technology, Pasadena, CA (US)

(72) Inventors: Morteza Gharib, Altadena, CA (US); Adrianus I. Aria, Pasadena, CA (US); Elijah Bodhi Sansom, San Francisco, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 25 days.

(21) Appl. No.: 13/762,197

(22) Filed: Feb. 7, 2013

(65) Prior Publication Data

US 2013/0158377 A1 Jun. 20, 2013

Related U.S. Application Data

(63) Continuation of application No. 12/657,862, filed on Jan. 27, 2010, now abandoned, which is a continuation-in-part of application No. 11/827,169, filed on Jul. 10, 2007, now Pat. No. 7,955,644.

(60) Provisional application No. 61/179,639, filed on May 19, 2009, provisional application No. 61/206,071, filed on Jan. 27, 2009.

(51) Int. Cl.
*A61M 5/00* (2006.01)
*A61M 37/00* (2006.01)
(Continued)

(52) U.S. Cl.
CPC ... *A61M 37/0015* (2013.01); *A61M 2037/0023* (2013.01); *A61M 2037/0053* (2013.01);
(Continued)

(58) Field of Classification Search
CPC .................. A61M 37/0015; A61M 2037/003; A61M 2037/0053; A61M 2037/0023; A61M 2037/0061; A61M 2205/0244; A61M 2037/0038; A61M 2037/0046
USPC ........ 604/96.01, 103.01, 103.02, 103.08, 173
See application file for complete search history.

(56) References Cited

U.S. PATENT DOCUMENTS

| 3,964,482 A | 6/1976 | Gerstel et al. |
| 4,842,390 A | 6/1989 | Sottini et al. |

(Continued)

FOREIGN PATENT DOCUMENTS

| EP | 1948562 B1 | 7/2010 |
| JP | 2006-114265 | 4/2006 |

(Continued)

OTHER PUBLICATIONS

PCT/US2012/069941, US, International Search Report/Written Opinion, Feb. 21, 2013.
(Continued)

*Primary Examiner* — Kevin C Sirmons
*Assistant Examiner* — William Carpenter
(74) *Attorney, Agent, or Firm* — One LLP (57) ABSTRACT

The present invention relates to a nano-enhanced device for substance transfer between the device and a tissue. The device comprises a substrate with substantially aligned carbon nanotubes anchored within the substrate, and with at least one end of the carbon nanotubes protruding from the substrate. The protruding nanotube ends may be coated with a drug for delivery of the drug into body tissue. The present invention may be incorporated into an angioplasty catheter balloon or into a patch that is worn on the skin. The carbon nanotubes can be grouped in clusters to effectively form nano-needles which can transfer fluid to or from the subdermal tissue. The nano-needles can be used in conjunction with a sensor to ascertain body fluid information such as pH, glucose level, etc.

4 Claims, 7 Drawing Sheets

(51) Int. Cl.
*A61K 47/48* (2006.01)
*A61L 27/44* (2006.01)
*A61L 27/54* (2006.01)
*A61L 27/56* (2006.01)
*B29C 70/64* (2006.01)
*B82Y 5/00* (2011.01)
*B82Y 30/00* (2011.01)
*B82Y 40/00* (2011.01)
*C01B 31/02* (2006.01)
*A61B 5/145* (2006.01)
*A61M 5/44* (2006.01)
*A61M 25/10* (2013.01)
*A61N 1/30* (2006.01)
*A61N 5/06* (2006.01)
*B29K 105/16* (2006.01)

(52) U.S. Cl.
CPC ......... *A61K47/48992* (2013.01); *A61L 27/443* (2013.01); *A61L 27/54* (2013.01); *A61L 27/56* (2013.01); *A61L 2300/258* (2013.01); *A61L 2300/416* (2013.01); *A61L 2300/602* (2013.01); *A61L 2300/606* (2013.01); *A61L 2400/12* (2013.01); *B29C 70/64* (2013.01); *B29K 2105/162* (2013.01); *B82Y 5/00* (2013.01); *B82Y 30/00* (2013.01); *B82Y 40/00* (2013.01); *C01B 31/0206* (2013.01); *A61B 5/14532* (2013.01); *A61M 5/44* (2013.01); *A61M 25/104* (2013.01); *A61M 37/0092* (2013.01); *A61N 1/306* (2013.01); *A61N 5/062* (2013.01)

(56) References Cited

U.S. PATENT DOCUMENTS

| | | | |
|---|---|---|---|
| 5,116,317 A | 5/1992 | Carson, Jr. et al. | |
| 5,457,041 A | 10/1995 | Ginaven et al. | |
| 6,256,533 B1 | 7/2001 | Yuzhakov et al. | |
| 6,334,856 B1 * | 1/2002 | Allen et al. | 604/191 |
| 6,379,324 B1 | 4/2002 | Gartstein et al. | |
| 6,471,903 B2 | 10/2002 | Sherman et al. | |
| 6,503,231 B1 | 1/2003 | Prausnitz et al. | |
| 6,533,949 B1 * | 3/2003 | Yeshurun et al. | 216/11 |
| 6,720,547 B1 | 4/2004 | Rajadhyaksha et al. | |
| 6,749,792 B2 | 6/2004 | Olson | |
| 6,866,801 B1 | 3/2005 | Mau et al. | |
| 6,924,335 B2 | 8/2005 | Fan et al. | |
| 7,037,562 B2 | 5/2006 | Jimenez | |
| 7,097,776 B2 | 8/2006 | Govinda Raju | |
| 7,160,620 B2 | 1/2007 | Huang et al. | |
| 7,183,003 B2 | 2/2007 | Leu et al. | |
| 7,235,442 B2 | 6/2007 | Wang et al. | |
| 7,291,396 B2 | 11/2007 | Huang et al. | |
| 7,393,428 B2 | 7/2008 | Huang et al. | |
| 7,396,477 B2 | 7/2008 | Hsiao | |
| 7,438,844 B2 | 10/2008 | Huang et al. | |
| 7,491,628 B2 | 2/2009 | Noca et al. | |
| 7,534,648 B2 | 5/2009 | Raravikar et al. | |
| 7,569,425 B2 | 8/2009 | Huang et al. | |
| 7,611,628 B1 | 11/2009 | Hinds, III | |
| 7,611,651 B2 | 11/2009 | Huang et al. | |
| 7,695,769 B2 | 4/2010 | Watanabe et al. | |
| 7,955,644 B2 | 6/2011 | Sansom et al. | |
| 8,043,250 B2 | 10/2011 | Xu | |
| 8,048,017 B2 | 11/2011 | Xu | |
| 8,062,573 B2 | 11/2011 | Kwon | |
| 8,257,324 B2 | 9/2012 | Prausnitz et al. | |
| 8,377,590 B2 | 2/2013 | Park et al. | |
| 2001/0023986 A1 | 9/2001 | Mancevski | |
| 2002/0155737 A1 | 10/2002 | Roy et al. | |
| 2003/0069548 A1 | 4/2003 | Connelly et al. | |
| 2003/0119920 A1 | 6/2003 | Wang et al. | |
| 2003/0180472 A1 | 9/2003 | Zhou et al. | |
| 2005/0011858 A1 | 1/2005 | Kuo et al. | |
| 2005/0029223 A1 | 2/2005 | Yeshurun et al. | |
| 2005/0067346 A1 | 3/2005 | Noack et al. | |
| 2005/0100960 A1 | 5/2005 | Dai et al. | |
| 2005/0127351 A1 | 6/2005 | Tolt | |
| 2005/0157386 A1 | 7/2005 | Greenwald et al. | |
| 2005/0167647 A1 | 8/2005 | Huang et al. | |
| 2005/0171480 A1 | 8/2005 | Mukerjee et al. | |
| 2005/0220674 A1 | 10/2005 | Shafirstein et al. | |
| 2005/0230082 A1 | 10/2005 | Chen | |
| 2005/0245659 A1 | 11/2005 | Chen | |
| 2006/0030812 A1 | 2/2006 | Golubovic-Liakopoulos et al. | |
| 2006/0057388 A1 * | 3/2006 | Jin et al. | 428/408 |
| 2006/0073712 A1 | 4/2006 | Suhir | |
| 2006/0084942 A1 | 4/2006 | Kim et al. | |
| 2006/0093642 A1 * | 5/2006 | Ranade | 424/423 |
| 2006/0118791 A1 | 6/2006 | Leu et al. | |
| 2006/0184092 A1 * | 8/2006 | Atanasoska et al. | 604/20 |
| 2006/0184112 A1 | 8/2006 | Horn et al. | |
| 2006/0226016 A1 | 10/2006 | S/O Govinda Raju et al. | |
| 2006/0231970 A1 | 10/2006 | Huang et al. | |
| 2006/0286305 A1 | 12/2006 | Thies et al. | |
| 2007/0053057 A1 | 3/2007 | Zust et al. | |
| 2007/0066934 A1 * | 3/2007 | Etheredge et al. | 604/46 |
| 2007/0066943 A1 | 3/2007 | Prasad et al. | |
| 2007/0081242 A1 | 4/2007 | Kempa et al. | |
| 2007/0099311 A1 * | 5/2007 | Zhou et al. | 438/5 |
| 2007/0114658 A1 | 5/2007 | Dangelo et al. | |
| 2007/0207182 A1 | 9/2007 | Weber et al. | |
| 2007/0244245 A1 | 10/2007 | Liu et al. | |
| 2007/0276330 A1 | 11/2007 | Beck et al. | |
| 2008/0009800 A1 | 1/2008 | Nickel | |
| 2008/0199626 A1 | 8/2008 | Zhou et al. | |
| 2008/0269666 A1 | 10/2008 | Wang et al. | |
| 2008/0292840 A1 | 11/2008 | Majumdar et al. | |
| 2008/0318049 A1 | 12/2008 | Hata et al. | |
| 2009/0032496 A1 | 2/2009 | Yao et al. | |
| 2009/0068387 A1 | 3/2009 | Panzer et al. | |
| 2009/0118662 A1 | 5/2009 | Schnall | |
| 2009/0130370 A1 | 5/2009 | Sansom et al. | |
| 2009/0208743 A1 | 8/2009 | Petit | |
| 2009/0269560 A1 | 10/2009 | Dhinojwala et al. | |
| 2010/0075024 A1 | 3/2010 | Ajayan et al. | |
| 2010/0196446 A1 | 8/2010 | Gharib et al. | |
| 2010/0247777 A1 | 9/2010 | Nikolaev et al. | |
| 2010/0253375 A1 | 10/2010 | Fang et al. | |
| 2010/0330277 A1 | 12/2010 | Ajayaghosh et al. | |
| 2011/0045080 A1 | 2/2011 | Powis et al. | |
| 2011/0233779 A1 | 9/2011 | Wada et al. | |
| 2011/0250376 A1 | 10/2011 | Aria et al. | |
| 2012/0021164 A1 | 1/2012 | Sansom et al. | |
| 2012/0058170 A1 | 3/2012 | Gharib et al. | |
| 2013/0178722 A1 | 7/2013 | Aria et al. | |

FOREIGN PATENT DOCUMENTS

| | | |
|---|---|---|
| JP | 2006-164835 | 6/2006 |
| TW | 253 898 | 4/2006 |
| TW | 256 877 | 6/2006 |
| WO | WO 96/21938 A1 | 7/1996 |
| WO | WO 2006/041535 A1 | 4/2006 |
| WO | PCT/US2008/012641 | 12/2009 |
| WO | PCT/US2007/015754 | 1/2010 |
| WO | PCT/US2007/015754 | 2/2010 |
| WO | PCT/US2008/012641 | 5/2010 |
| WO | WO 2010/087971 A2 | 8/2010 |
| WO | WO 2010/120564 A2 | 10/2010 |
| WO | PCT/US2010/000243 | 11/2010 |
| WO | PCT/US2010/000243 | 8/2011 |
| WO | PCT/US2011/031465 | 12/2011 |
| WO | WO 2013/090844 A1 | 6/2013 |
| WO | PCT/US2013/052580 | 10/2013 |
| WO | PCT/US2012/069941 | 6/2014 |

OTHER PUBLICATIONS

Ajayan, P.M., et al., "Aligned Carbon Nanotube Arrays Formed by Cutting a Polymer Resin-Nanotube Composite", Science, vol. 265, No. 5176, Aug. 1994, pp. 1212-1214.

(56) References Cited

OTHER PUBLICATIONS

Anderson, A., et al., "High sensitivity assays for docetaxel and paclitaxel in plasma using solid-phase extraction and high-performance liquid chromatography with UV detection", BMC Clinical Pharmacology, Jan. 2006, vol. 6, Issue 2, pp. 1-10.
Arakawa, K., et al., "Fluorescence Analysis of Biochemical Constituents Identifies Atherosclerotic Plaque With a Thin Fibrous Cap", Arterioscler. Thromb. Vasc. Biol., 2002, vol. 22, pp. 1002-1007.
Aria, A.I., et al., "Reversible Tuning of the Wettability of Carbon Nanotube Arrays: The Effect of Ultraviolet/Ozone, and Vacuum Pyrolysis Treatments", Langmuir, 2011, vol. 27, pp. 9005-9011.
Arifin, D.Y., et al., "Role of Convective Flow in Carmustine Delivery to a Brain Tumor", Pharmaceutical Research, 2009, pp. 1-14.
Barber, A.H., et al., "Static and Dynamic Wetting Measurements of Single Carbon Nanotubes", Physical Review Letters, vol. 92, No. 18, May 2004, pp. 186103-1-186103-4.
Boldor, D., et al., "Temperature Measurement of Carbon Nanotubes Using Infrared Thermography", Chem. Matter. vol. 20, No. 12, 2008, pp. 4011-4016.
Boo, H., et al., "Electrochemical Nanoneedle Biosensor Based on Multiwall Carbon Nanotube", Anal. Chem., vol. 78, No. 2, 2006, pp. 617-620.
Borca-Tasciuc, T., et al., "Anisotropic Thermal Diffusivity Characterization of Aligned Carbon Nanotube-Polymer Composites", Journal of Nanoscience and Nanotechnology, vol. 7, No. 4, 2007, pp. 1581-1588.
Boyea, J.M. et al., "Carbon Nanotube-Based Supercapacitors: Technologies and Markets", Nanotechnology Law & Business, Mar. 2007, vol. 4, No. 1, pp. 585-593.
Bronikowski, M.J., "CVD growth of carbon nanotube bundle arrays", Carbon, 2006, vol. 44, pp. 2822-2832.
Bronikowski, M.J., "Longer Nanotubes at Lower Temperatures: The Influence of Effective Activation Energies on Carbon Nanotube Growth by Thermal Chemical Vapor Deposition", J. Phys. Chem. C, vol. 111, No. 48, 2007, pp. 17705-17712.
Celermajer, D.S., "Understanding the pathophysiology of the arterial wall: which method should we choose?", European Heart Journal Supplements, 2002, vol. 4, Supplement F, pp. F24-F28.
Chen, Chuan-Hua, et al., "Dropwise condensation on superhydrophobic surfaces with two-tier roughness", Appl. Phys. Ltrs., 2007, vol. 90, pp. 173108-1-173108-3.
Chen, J., et al., "Functionalized Single-Walled Carbon Nanotubes as Rationally Designed Vehicles for Tumor-Targeted Drug Delivery", J. Am. Chem. Soc., 2008, vol. 130, pp. 16778-16785.
Cheng, Li et al., "A fullerene-single wall carbon nanotube complex for polymer bulk heterojunction photovoltaic cells", J. Matter. Chem., 2007, vol. 17, pp. 2406-2411.
Choi, T.Y., et al., "Measurement of thermal conductivity of individual multiwalled carbon nanotubes by the 3-$\omega$ method", Appl. Phys. Letters, vol. 87, No. 1, 2005, pp. 013108-1-013108-3.
Conway, B.E., "Electromechanical Supercapacitors: Scientific Fundamentals and Technological Applications", Chapter 2-Similarities and Differences between Supercapacitors and Batteries for Storing Electrical Energy, 1999, pp. 11-31.
Correa-Duarte, M.A., et al., "Fabrication and Biocompatibility of Carbon Nanotube-Based 3D Networks as Scaffolds for Cell Seeding and Growth", Nano Letters, 2004, vol. 4, No. 11, pp. 2233-2236.
Correa-Duarte, M.A., et al., "Nanoengineered Polymeric Thin Films by Sintering CNT-Coated Polystyrene Spheres", Small, vol. 2, No. 2, 2006, pp. 220-224.
Crabtree, G.W., et al., "Solar energy conversion", Physics Today, vol. 60, No. 3, 2007, pp. 37-42.
Creel, C.J., et al., "Arterial Paclitaxel Distribution and Deposition", Circ. Res., vol. 86, No. 8, 2000, pp. 879-884.
Cui, D., et al., "Effect of single wall carbon nanotubes on human HEK293 cells", Toxicology Letters, 2005, vol. 155, pp. 73-85.
Dai, L., et al., "Functionalized surfaces based on polymers and carbon nanotubes for some biomedical and optoelectronic applications", Nanotechnology, vol. 14, No. 10, 2003, pp. 1084-1097.
Daniello, R.J., et al., "Drag reduction in turbulent flows over superhydrophobic surfaces", Physics of Fluids, 2009, vol. 21, pp. 085103-1-085103-9.

Daraio, C., et al., "Highly nonlinear contact interaction and dynamic energy dissipation by forest of carbon nanotubes", Appl. Phys. Ltrs., vol. 85, No. 23, pp. 5724-5726.
Davies, M.J., "The Composition of Coronary-Artery Plaques", The New England Journal of Medicine, 1997, vol. 336, No. 18, pp. 1312-1314.
Davis, S. P., et al., "Insertion of microneedles into skin: measurement and prediction of insertion force and needle fracture force", Journal of Biomechanics, 2004, vol. 34, pp. 1155-1163.
Detter, C., et al., "Fluorescent Cardiac Imaging : A Novel Intraoperative Method for Quantitative Assessment of Myocardial Perfusion During Graded Coronary Artery Stenosis", Circulation, 2007, vol. 116, pp. 1007-1014.
Diaz, J.F., et al., "Macromolecular Accessibility of fluorescent Taxoids Bound at a Paclitaxel Binding Site in the Microtubule Surface", J. Biol. Chem., 2005, vol. 280, No. 5, pp. 3928-3937.
Elias, K.L., et al., "Enhanced functions of osteoblasts on nanometer diameter carbon fibers", Biomaterials, 2002, vol. 23, pp. 3279-3287.
Falvo, M.R., et al., "Bending and buckling of carbon nanotubes under large strain", Nature, vol. 389, 1997, pp. 582-584.
Fan, S., et al., "Self-Oriented Regular Arrays of Carbon Nanotubes and Their Field Emission Properties", Science, vol. 283, Jan. 1999, pp. 512-514.
Firkowska, I. et al., Highly Ordered MWNT-Based Matrixes: Topography at the Nanoscale Conceived for Tissue Engineering, Langmuir, vol. 22, 2006, pp. 5427-5434.
Frank, S., et al., "Carbon Nanotube Quantum Resistors", Science, vol. 280, 1998, pp. 1744-1746.
Futaba, D.N., et al., "Shape-engineerable and highly densely packed single-walled carbon nanotubes and their application as super-capacitor electrodes", Nature Materials, 2006, vol. 5, pp. 987-994.
Gabay, T., et al., Engineered self-organization of neural networks using carbon nanotube clusters Physica A, 2005, vol. 350, pp. 611-621.
Glazachev, Y.I., "Fluorescence Photobleaching Recovery Method with Pulse-Position Modulation of Bleaching/Probing Irradiation", J. Fluoresc., 2009, vol. 19, No. 5, pp. 875-880.
Guittet, M., et al., "Use of Vertically-Aligned Carbon Nanotube Array to Enhance the Performance of Electrochemical Capacitors", Proceedings of the 11th International Conference on Nanotechnology IEEE, 2011, pp. 1-6.
Haggenmueler, R., et al., "Aligned single-wall carbon nanotubes in composites by melt processing methods", Chemical Physical Letters, vol. 330, 2000, pp. 219-225.
Han, Z.J., et al., "Superhydrophobic amorphous carbon/carbon nanotube nanocomposites", Applied Physics Letters, 2009, vol. 94, pp. 223106-1-223106-3.
Haq, M.I., et al., "Clinical administration of microneedles: skin puncture, pain and sensation", Biomedical Microdevices, 2009, vol. 11, pp. 35-47.
Hart, A.J., et al., "Rapid Growth and Flow-Mediated Nucleation of Millimeter-Scale Aligned Carbon Nanotube Structures from a Thin-Film Catalyst", J. Phys. Chem. B, 2006, vol. 110, pp. 8250-8257.
Hattori, H., et al., "A Novel Real-Time Fluorescent Optical Imaging System in Mouse Heart, A Powerful Tool For Studying Coronary Circulation and Cardiac Function", Circ Cardiovasc Imaging, 2009, vol. 2, pp. 277-278.
Hearn, E.M., et al., "Transmembrane passage of hydrophobic compounds through a protein channel wall", Nature, 2009, vol. 458, pp. 367-371.
Hinds, B.J., et al., "Aligned Multiwalled Carbon Nanotube Membranes", Science, vol. 303, 2004, pp. 62-65.
Holzapfel, G.A., et al., "Anisotropic Mechanical Properties of Tissue Components in Human Atherosclerotic Plaques", J. Bio. Eng., 2004, vol. 126, pp. 657-665.
Hong, Y.C., et al., "Superhydrophobicity of a material made from multiwalled carbon nanotubes", Applied Physics Letters, 2006, vol. 88, pp. 24401-1-24401-3.
Hosono, M. et al., "Intraoperative fluorescence imaging during surgery for coronary artery fistula", Interact CardioVasc Thorac Surg, 2010, vol. 10, pp. 476-477.
Hu, H., et al., "Chemically Functionalized Carbon Nanotubes as Substrates for Neuronal Growth", Nanoletters, 2004, vol. 4, No. 3, pp. 507-511.

(56) References Cited

OTHER PUBLICATIONS

Huang, H., et al., "Aligned Carbon Nanotube Composite Films for Thermal Management", Advanced Materials, vol. 17, No. 13, 2005, pp. 1652-1656.

Huang, L., et al., "Stable Superhydrophobic Surface via Carbon Nanotubes Coated with a ZnO Thin Film", J. Phys. Chem. B, 2005, vol. 109, pp. 7746-7748.

Huang, X., et al., "Inherent-opening-controlled pattern formation in carbon nanotube arrays", Nanotechnology, vol. 18, 2007, pp. 1-6.

Huber, C.A., et al, "Nanowire Array Composites", Science, vol. 263, 1994, pp. 800-802.

Huczko, A., et al., "Carbon Nanotubes: Experimental Evidence for a Null Risk of Skin Irritation and Allergy?", Fullerene Science and Technology, 2001, vol. 9, No. 2, pp. 247-250.

Huczko, A., et al., "Physiological Testing of Carbon Nanotubes: Are They Asbestos-Like?", Fullerene Science and Technology, 2001, vol. 9, No. 2, pp. 251-254.

Huczko, A., et al., "Pulmonary Toxicity of 1-D Nanocarbon Materials", Fullerenes, Nanotubes, and Carbon Nanostructures, 2005, vol. 13, pp. 141-145.

Ijima, S., "Helical microtubules of graphitic carbon", Nature, vol. 354, 1991, pp. 56-58.

Jia, G., et al., "Cytotoxicity of Carbon Nanomaterials: Single-Wall Nanotube, Multi-Wall Nanotube, and Fullerene", Environ. Sci. Technol., 2005, vol. 39, pp. 1378-1383.

Jin, L., et al., "Alignment of carbon nanotubes in a polymer matrix by mechanical stretching", Applied Physics Letters, vol. 73, No. 9, 1998, pp. 1197-1199.

Jousseaume, V., et al., "Few graphene layers/carbon nanotube composites grown at complementary-metal-oxide-semiconductor compatible temperature", Applied Physics Letters, 2011, vol. 98, pp. 12103-1-12103-3.

Jung, Y.J., et al., "Aligned Carbon Nanotube-Polymer Hybrid Architectures for Diverse Flexible Electronic Applications", Nanoletters, vol. 6, No. 3, 2006, pp. 413-418.

Kam, N.W.S., et al., "Carbon nanotubes as multifunctional biological transporters and near-infrared agents for selective cancer cell destruction", PNAS, vol. 102, No. 33, 2005, pp. 11600-11605.

Kaushik, S., et al., "Lack of Pain Associated with Microfabricated Microneedles", Anesthesia & Analgesia, 2001, vol. 92, pp. 502-504.

Kazaoui, S., et al., "Near-infrared photoconductive and photovoltaic devices using single-wall carbon nanotubes in conductive polymer films", Journal of Applied Physics, 2005, vol. 98, pp. 084314-1-084314-6.

Kim, P., et al., "Thermal Transport Measurements of Individual Multiwalled Nanotubes", Physical Review Letters, vol. 87, No. 21, 2001, pp. 215502-1-2015502-4.

Kim, Yeu-Chun, et al., "Microneedles for drug and vaccine delivery", Adv. Drug Delivery Reviews, 2012, vol. 64, No. 14, pp. 1547-1568.

Kim, Youn-Su, et al., "Out-of-plane growth of CNTs on grapheme for supercapacitor applications", Nanotechnology, 2012, vol. 23, pp. 1-7.

Kondo, D., et al., "Self-organization of Novel Carbon Composite Structure: Graphene Multi-Layers Combined Perpendicularly with Aligned Carbon Nanotubes", Applied Physics Express, 2008, vol. 1, No. 7, pp. 074003-1-074003-3.

Kopterides, P., et al., "Statins for sepsis: a critical and updated review", Clin Microbiol Infect, 2009, vol. 15, No. 4, pp. 325-334.

Krishnan, A., et al., "Young's modulus of single-walled nanotubes", Physical Review B, 1998, vol. 58, No. 20, pp. 14013-14015.

Lahiff, E., et al., "Selective Positioning and Density Control of Nanotubes within a Polymer Thin Film", Nanoletters, vol. 3, No. 10, 2003, pp. 1333-1337.

Lam, C.W., et al., "Pulmonary Toxicity of Single-Wall Carbon Nanotubes in Mice 7 and 90 Days After Intratracheal Instillation", Toxicol Sciences, 2004, vol. 77, pp. 126-134.

Lau, K., et al., "Superhydrophobic Carbon Nanotube Forests", Nanoletters, 2003, vol. 3, No. 12, pp. 1701-1705.

Lee, C., et al., "Measurement of the Elastic Properties and Intrinsic Strength of Monolayer Graphene", Science, 2008, vol. 321, pp. 385-388.

Lee, J.U., "Photovoltaic effect in ideal carbon nanotube diodes", Applied Physics Letters, vol. 87, No. 7, 2005, pp. 073101-1-073101-3.

Li, S., et al., "Super-Hydrophobicity of Large-Area Honeycomb-Like Aligned Carbon Nanotubes", J. Phys. Chem. B, 2002, vol. 106, pp. 9274-9276.

Li, W.Z., et al., "Large-Scale Synthesis of Aligned Carbon Nanotubes", Science, vol. 274, 1996, pp. 1701-1703.

Li, H., et al., "Super-"Amphiphobic" Aligned Carbon Nanotube Films", Angew. Chem. Int. Ed., 2001, vol. 40, No. 9, pp. 1743-1746.

Liu, Z., et al., "Drug delivery with carbon nanotubes for in vivo cancer treatment", Cancer Res., 2008, vol. 68, No. 16, pp. 6652-6660.

Lovich, M.A., et al., "Carrier Proteins Determine Local Pharmacokinetics and Arterial Distribution of Paclitaxel", J. Pharm. Sci., 2001, vol. 90, No. 9, pp. 1324-1335.

Lu, J.P., et al., "Carbon Nanotubes and Nanotube-Based Nano Devices", Int. J. Hi. Spe. Ele. Syst., 1998, vol. 9, No. 1, pp. 101-123.

Lyon, B., et al., "Carbon Nanotube Micro-needles for Rapid Transdermal Drug Delivery", APS DFD Meeting, San Diego, CA, Nov. 18, 2012.

Lyon, B., et al., "Feasibility Study of CNT for Rapid transdermal Drug Delivery", Mater. Res. Soc. Symp. Proc., 2013, vol. 1569, pp. 239-244.

Lyon, B., et al., "Feasibility Study of Carbon Nanotube Microneedles for Rapid Transdermal Drug Delivery", MRS Spring Meeting, San Francisco, CA, Apr. 2013.

Lyon, B., et al., "Carbon Nanotube—Polyimide Composite Microneedles for Rapid Transdermal Drug Delivery", Society of Biomaterials Meeting, Boston, MA, Apr. 2013.

Mamedov, A.A., et al., "Molecular design of strong single-wall carbon nanotube/polyelectrolyte multilayer composites", Nature Materials, 2005, vol. 1, No. 3, pp. 190-194.

Manohara, H.M., et al., "High-current-density field emitters based on arrays of carbon nanotube bundles", J. Vac. Sci. Tech B, 2005, vol. 23, No. 1, pp. 157-161.

McKenzie, J.L., et al., "Decreased functions of astrocytes on carbon nanofiber materials", Biomaterials, 2004, vol. 25, pp. 1309-1317.

Melechko, A.V., et al., "Vertically aligned carbon nanofibers and related structures: Controlled synthesis and directed assembly", Journal of Applied Physics, vol. 97, No. 4, 2005, pp. 041301-1-041301-39.

Men, X.H., et al., "Superhydrophobic/superhydrophilic surfaces from a carbon nanotube based composite coating", Applied Physics A, 2009, pp. 1-6.

Migliavacca, F., et al., "Expansion and drug elution model of a coronary stent", Comput Methods Biomech Biomed Engin, 2007, vol. 10, No. 1, pp. 63-73.

Min, T., et al., "Effects of hydrophobic surface on skin-friction drag", Physics of Fluids, 2004, vol. 16, No. 7, pp. L55-L58.

Monteiro-Riviere, N.A., et al., "Multi-walled carbon nanotube interactions with human epidermal keratinocytes", Toxicol Letters, 2005, vol. 155, pp. 377-384.

Morjan, R.E., et al., "High growth rates and wall decoration of carbon nanotubes grown by plasma-enhanced chemical vapour deposition", Chemical Physics Letters, vol. 383, 2004, pp. 385-390.

Muller, J., et al., "Respiratory toxicity of multi-wall carbon nanotubes", Toxicol Appl Pharmacol, 2005, vol. 207, pp. 221-231.

Nerushev, O.A., et al., "The temperature dependence of Fe-catalysed growth of carbon nanotubes on silicon substrates", Physica B, vol. 323, 2002, pp. 51-59.

Nessim, G.D., et al., "Tuning of Vertically-Aligned Carbon Nanotube Diameter and Area Density through Catalyst Pre-Treatment", Nano Letters., 2008, vol. 8, No. 11, pp. 3587-3593.

Noca, F., et al., "NanoWicks: Nanofiber-Patterned Surfaces for Passive Fluid Transport, Nanopumping, Ultrafiltration, Nanomixing, and Fluidic Logic", NASA Tech Briefs, 2007, pp. 1-7.

Oreopoulos, J., et al., "Combinatorial microscopy for the study of protein—membrane interactions in supported lipid bilayers: Order parameter measurements by combined polarized TIRFM/AFM", J. Struct. Biol., 2009, vol. 168, pp. 21-36.

(56) References Cited

OTHER PUBLICATIONS

Panchagnula, R., et al., "Effect of Lipid Bilayer Alteration on Transdermal Delivery of a High-Molecular-Weight and Lipophilic Drug: Studies with Paclitaxel", J. Pharm. Sci., 2004, vol. 93, No. 9, pp. 2177-2183.
Pandolfo, A.G., et al., "Carbon properties and their role in supercapacitors", Journal of Power Sources, 2006, vol. 157, pp. 11-27.
Parekh, H., et al., "The Transport and Binding of Taxol", Gen. Pharmac., 1997, vol. 29, No. 2, pp. 167-172.
Pernodet, N., et al., "Pore size of agarose gels by atomic force microscopy", Electrophoresis, 1997, vol. 18, pp. 55-58.
Prausnitz, M.R., et al., "Transdermal drug delivery", Nature Biotechnology, 2008, vol. 26, No. 11, pp. 1261-1268.
Price, R.L., et al., "Selective bone cell adhesion on formulations containing carbon nanofibers", Biomaterials, 2003, vol. 24, pp. 1877-1887.
Raravikar, N.R., et al., "Synthesis and Characterization of Thickness-Aligned Carbon Nanotube-Polymer Composite Films", Chem. Mater., vol. 17, No. 5, 2005, pp. 974-983.
Raravikar, N.R., et al., "Embedded Carbon-Nanotube-Stiffened Polymer Surfaces", Small, vol. 1, No. 3, 2005, pp. 317-320.
Ren, Z.F., et al., "Synthesis of Large Arrays of Well-Aligned Carbon Nanotubes on Glass", Science, vol. 282, 1998, pp. 1105-1107.
Roxhed, N., et al., "Painless Drug Delivery Through Microneedle-Based Transdermal Patches Featuring Active Infusion", IEEE Transactions on Biomedical Engineering, 2008, vol. 55, No. 3, pp. 1063-1071.
Ruoff, R.S., et al., "Is $C_{60}$ stiffer than diamond?", Nature, 1991, vol. 350, pp. 663-664.
Sansom, E.B., "Experimental Investigation on Patterning of Anchored and Unanchored Aligned Carbon Nanotube Mats by Fluid Immersion and Evaporation", PhD Thesis, California Institute of Technology, Pasadena, CA, 2007.
Sansom, E.B., et al., "Controlled partial embedding of carbon nanotubes within flexible transparent layers", Nanotechnology, vol. 19, No. 3, 2008, pp. 1-6.
Scheller, B., et al., "Paclitaxel Balloon Coating, a Novel Method for Prevention and Therapy of Restenosis", Circulation, vol. 110, No. 7, 2004, pp. 810-814.
Scheuplein, R.J., et al., "Permeability of the Skin", Physiological Reviews, 1971, vol. 51, No. 4, pp. 702-747.
Scheuplein, R.J., Chapter 19: Permeability of the skin, Handbook of Physiology-Reactions to Environmental Agents, 2011, pp. 299-322.
Sethi, S., et al., "Gecko-Inspired Carbon Nanotube-Based Self-Cleaning Adhesives", Nanoletters, vol. 8, No. 3, 2008, pp. 822-825.
Shvedova, A.A., et al., "Exposure to Carbon Nanotube Material: Assessment of Nanotube Cytotoxicity Using Human Keratinocyte Cells", J. Toxicol. Environ. Health, Pat A, 2003, vol. 66, pp. 1909-1926.
Sinha, N., et al., "Carbon Nanotubes for Biomedical Applications", IEEE Transactions on Nanobioscience, vol. 4, No. 2, 2005, pp. 180-195.
Suh, J.S., et al., "Highly ordered two-dimensional carbon nanotube arrays", Applied Physics Letters, vol. 75, No. 14, 1999, pp. 2047-2049.
Talapatra, S., et al., "Direct Growth of Aligned Carbon Nano-tubes on Bulk Metals", Nature Nanotechnology, 2006, vol. 1, pp. 112-116.
Tamura, K., et al., "Effects of Micro/Nano Particle Size on Cell Function and Morphology", Key Engineering Materials, 2004, vols. 254-256, pp. 919-922.
Tanaka, E., et al., "Real-Time Assessment of Cardiac Perfusion, Coronary Angiography, and Acute Intravascular Thrombi Using Dual-Channel Near-Infrared Fluorescence Imaging", Thorac Cardiovasc Surg., 2009, vol. 138, No. 1, pp. 133-140.
Tepe, G., et al., "Paclitaxel-coated Angioplasty Catheters for Local Drug Delivery", Touch Briefings-Interventional Cardiology, 2007, pp. 61-63.
Tian, B., et al., "Coaxial silicon nanowires as solar cells and nanoelectronic power sources", Nature, vol. 449, 2007, pp. 885-888.
Veedu, V.P., et al., "Multifunctional composites using reinforced laminae with carbon nanotube forests", Nature Materials, 2006, vol. 5, pp. 457-462.
Wagner, H.D., et al., "Stress-induced fragmentation of multiwall carbon nanotubes in a polymer matrix", Applied Physics Letters, vol. 72, No. 2, 1998, pp. 188-190.
Wang, G.X., et al., "Growth and Lithium Storage Properties of Vertically Aligned Carbon Nanotubes", Metals and Materials Intl., 2006, vol. 12, No. 5, pp. 413-416.
Wang, Z., et al., "Impact dynamics and rebound of water droplets on superhydrophobic carbon nanotube arrays", Applied Physics Letters, 2007, vol. 91, pp. 023105-1-023105-3.
Wardle, B.L., et al., "Fabrication and Characterization of Ultrahigh-Volume-Fraction Aligned Carbon Nanotube-Polymer Composites", Adv. Mater., 2008, vol. 20, pp. 2707-2714.
Warheit, D.B., et al., "Comparative Pulmonary Toxicity Assessment of Single-wall Carbon Nanotubes in Rats", Toxicol. Sciences, 2004, vol. 77, pp. 117-125.
Waseda, K., et al., "Intraoperative Fluorescence Imaging System for On-Site Assessment of Off-Pump Coronary Artery Bypass Graft", JACC: CardioVasc Imaging, 2009, vol. 2, No. 5, pp. 604-612.
Webster, T.J., et al., "Nano-biotechnology: carbon nanofibres as improved neural and orthopaedic implants", Nanotechnology, 2004, vol. 15, pp. 48-54.
Wermeling, D.P., et al., "Microneedles permit transdermal delivery of a skin-impermeant medication to humans", PNAS, 2008, vol. 105, No. 6, pp. 2058-2063.
Wong, E.W., et al., "Nanobeam Mechanics: Elasticity, Strength, and Toughness of Nanorods and Nanotubes", Science, vol. 277, 1997, pp. 1971-1975.
Wu, W., et al., "Covalently Combining Carbon Nanotubes with Anti-cancer Agent: Preparation and Antitumor Activity", ACS Nano, 2009, vol. 3, No. 9, pp. 2740-2750.
Zhu, L., et al., "Superhydrophobicity om Two-Tier Rough Surfaces Fabricated by Controlled Growth of Algined Carbon Nanotube Arrays Coated with Fluorocarbon", Langmuir, 2005, vol. 21, pp. 11208-11212.
Xie, Xl, et al., "Dispersion and alignment of carbon nanotubes in polymer matrix: A review", Mat. Science and Engineering R, vol. 49, No. 4, 2005, pp. 89-112.
Xu, J., et al., "Enhanced Thermal Contact Conductance Using Carbon Nanotube Array Interfaces", IEEE Transactions on Components and Packaging Technologies, 2006, vol. 29, No. 2, pp. 261-267.
Xu, Z., et al., "Multiwall Carbon Nanotubes Made of Monochirality Graphite Shells", J. Am. Chem. Soc., vol. 128, No. 4, 2006, pp. 1052-1053.
Yang, D, et al., "Hydrophilic multi-walled carbon nanotubes decorated with magnetite nanoparticles as lymphatic targeted drug delivery vehicles", Chem. Commun., 2009, pp. 4447-4449.
Yang, Zp, et al., "Experimental Observation of an Extremely Dark Material Made by a Low-Density Nanotube Array", Nanoletters, vol. 8, No. 2, 2008, pp. 446-451.
Yurdumakan, B., et al., "Synthetic gecko foot-hairs from multiwalled carbon nanotubes", Chem. Comm., vol. 30, 2005, pp. 3799-3801.
Zhang, L., et al., "Single-Walled Carbon Nanotube Pillars: a Superhydrophobic Surface", Langmuir, 2009, vol. 25, No. 8, pp. 4792-4798.
Zhang, L.L., et al., "Graphene-based materials as supercapacitor electrodes", J. Matter. Chem., 2010, vol. 20, pp. 5893-5992.
Zhao, L., et al., "Porous Silicon and Alumina as Chemically Reactive Templates for the Synthesis of Tubes and Wires of SnSe, Sn, and SnO2", Angew. Chem. Int. Ed., vol. 45, 2006, pp. 311-315.
Zhou, J.J., et al., "Flow conveying and diagnosis with carbon nanotube arrays", Nanotechnology, vol. 17, No. 19, 2006, pp. 4845-4853.
Zilberman, M., et al., "Paclitaxel-eluting composite fibers: Drug release and tensile mechanical properties", J. Biomed. Mater, Res., 2008, vol. 84A, pp. 313-323.

\* cited by examiner

DRUG DELIVERY AND SUBSTANCE TRANSFER FACILITATED BY NANO-ENHANCED DEVICE HAVING ALIGNED CARBON NANOTUBES PROTRUDING FROM DEVICE SURFACE

PRIORITY CLAIM

This is a continuation of U.S. patent application Ser. No. 12/657,862, filed on Jan. 27, 2010, entitled "DRUG DELIVERY AND SUBSTANCE TRANSFER FACILITATED BY NANO-ENHANCED DEVICE HAVING ALIGNED CARBON NANOTUBES PROTRUDING FROM DEVICE SURFACE," which is hereby incorporated by reference in its entirety. This application is also a continuation-in-part of U.S. patent application Ser. No. 11/827,169, filed on Jul. 10, 2007, entitled "METHOD FOR SELECTIVELY ANCHORING LARGE NUMBERS OF NANOSCALE STRUCTURES." This application also is a non-provisional patent application claiming benefit of priority of U.S. Provisional Application No. 61/206,071, filed on Jan. 27, 2009, entitled "CARBON NANOTUBE-BASED DEVICE FOR SUB-DERMAL BLOOD AND FLUID PROPERTY MONITORING," and U.S. Provisional Application No. 61/179,639, filed on May 19, 2009, entitled, "METHOD, DEVICE AND DESIGN FOR DELIVERY OF DRUGS BY A NANO-ENHANCED ANGIOPLASTY BALLOON."

FIELD OF INVENTION

The present invention relates to a nanostructure-enhanced drug delivery and blood monitoring device and, more particularly, to a device with aligned carbon nanotubes protruding from the device surface for facilitating drug or fluid transfer between the device and body tissue.

BACKGROUND OF INVENTION

Microvasculatures in the sub-dermal layer, if accessed, provide vital information about the health of the measured individual. For example, blood-glucose level, oxygen content, hormonal concentration, etc., can be directly measured from blood properties. Often to achieve this information, the skin must be penetrated by a needle in order to draw the blood into a sampling device. Use of such a needle is typically associated with pain, exposure of the blood to the environment, or risk of infection due to the rupture of the skin. A less invasive alternative to this procedure is to have a sensor embedded within the sub-dermal layer. Again, this procedure (depending on the scale) to achieve the implant is problematic both due to the process of placing the implant and the potential rejection by the patient's body.

Another area relevant to the subject matter of the present invention is in angioplasty procedures. Percutaneous transluminal angioplasty (PTA) and percutaneous transluminal coronary angioplasty (PTCA) are established, proven methods for re-opening stenotic or occluded arteries in a minimally invasive way. A balloon is placed in the stenotic segment of the artery using a catheter and then expanded until the lumen reaches its desired diameter. The use of an expanded balloon to forcibly open the narrowed section of the artery requires very high pressure (15 bars) and tends to cause injury to the vessel walls. The body's natural response to such injury is hyperproliferation, an abnormally high rate of cell division, which results in lumen narrowing and thus decreased function of the vessel. This is counterproductive to the initial goal of opening the stenotic or occluded artery.

To counter the hyperproliferation response of the vessel, an antiproliferative taxane drug such as paclitaxel may be used. A single, short contact of tissue with a small dose of paclitaxel has been shown to inhibit local cell proliferation. Paclitaxel is a mitotic inhibitor often used in cancer chemotherapy because cancerous cells exhibit hyperproliferation. Paclitaxel was originally derived from the bark of Pacific yew trees, but is now produced from other bioengineering methods. The mechanism of action of paclitaxel is the stabilization of microtubules through binding to tubulin, thus interfering with their normal breakdown during cell division. This has the net effect of reduced cell division rates, and counteracts hyperproliferation.

Antiproliferative taxanes have important properties for minimizing the hyperproliferation response of damaged vessel walls. They have high lipophilicity (hydrophobicity) and bind tightly to various cell constituents, giving good local retention at the delivery site. Though hydrophilic compounds penetrate easily into tissues, they also clear quickly. Paclitaxel is a hydrophobic compound and diffuses into the arterial wall from the lumen where it is delivered (See Literature Reference No. 1).

A typical procedure for treating a stenotic or occluded artery is to use a paclitaxel-coated angioplasty balloon, with the paclitaxel serving its purpose of inhibiting hyperproliferation following the balloon opening process. The major limitations on this process are the following:

1. The need of long inflation time in order to make sure the paclitaxel diffusion to the arterial wall is sufficient, which may cause excessive arterial wall injury. Previous study shows that 40-60 minutes are required to transfer roughly 90% of the initial dose of paclitaxel to the arterial wall (See Literature Reference No. 1);

2. In order to obtain the optimum benefit of hyperproliferation inhibition, it is important that the paclitaxel coating is not lost or washed off by the blood stream while advancing into the stenotic segment of the artery. Previous study shows that the rate of paclitaxel being washed away from the uninflated balloon by the blood stream is up to 1.2% from the initial dose per minute (See Literature Reference No. 2);

3. Potential loss of paclitaxel coating due to contact with the healthy arterial wall while advancing into the stenotic segment of the artery; and 4. The maximum dose of paclitaxel that can be applied on a single balloon is around 11 mg (10 $\mu g/mm^2$), which is significantly less than the paclitaxel dose approved by the FDA for Taxol (See Literature Reference No. 1).

It should be noted that the use of carbon nanotubes for the purpose of reinforcing the material properties of a balloon catheter has been suggested in U.S. Pat. No. 7,037,562. However, in that patent, the carbon nanotubes were mixed with the base material for the purpose of strengthening the material and not for drug delivery purposes. In addition, the carbon nanotubes were not aligned or partially anchored in the base material in a way such that they would protrude from the surface and facilitate drug delivery, rendering the device non-functional for that purpose.

Thus, a continuing need exists for a minimally invasive blood monitoring device which protects the extracted fluid from the atmosphere, and also for a drug delivery system which can effectively deliver high amounts of a desired drug to an affected site in a relatively short time period with minimal drug loss to passing body fluids.

The following references are cited throughout this application. For clarity and convenience, the references are listed herein as a central resource for the reader. The following references are hereby incorporated by reference as though fully included herein. The references are cited in the application by referring to the corresponding literature reference number.
(1) Creel, C. J., M. A. Lovich, and E. R. Edelman, *Arterial paclitaxel distribution and deposition.* Circulation Research, 2000. 86(8): p. 879-884.
(2) Scheller, B., U. Speck, C. Abramjuk, U. Bernhardt, M. Bohm, and G. Nickenig, *Paclitaxel balloon coating, a novel method for prevention and therapy of restenosis.* Circulation, 2004. 110(7): p. 810-814.
(3) Bronikowski, M. J., Longer nanotubes at lower temperatures: *The influence of effective activation energies on carbon nanotube growth by thermal chemical vapor deposition.* Journal of Physical Chemistry C, 2007. 111(48): p. 17705-17712.

SUMMARY OF INVENTION

The present invention relates to a nano-enhanced device for substance transfer between the device and a tissue. In one aspect, the device comprises a substrate and an array of substantially aligned carbon nanotubes having two ends, the carbon nanotubes being anchored within the substrate with at least one end protruding from the substrate, whereby the protruding carbon nanotubes enhance the substance transfer capabilities of the device.

In another aspect of the device, the carbon nanotube array is coated with a substance selected from the group consisting of a drug and a gene.

In yet another aspect of the device, the protruding ends of the anchored carbon nanotubes are free of coated drug and the drug coating area consists of an area selected from the group consisting of side walls of the carbon nanotubes and free spaces between the carbon nanotubes.

In another aspect, the device type is selected from the group consisting of a patch to be worn on the tissue and an angioplasty balloon.

In a further aspect of the device, the coated drug is paclitaxel.

In another aspect of the device, delivery of the drug from the device to the tissue is enhanced by a method selected from the group consisting of direct or indirect heating of at least a portion of the carbon nanotube array, electrical current through at least a portion of the carbon nanotube array, laser or other optical stimulation of at least a portion of the carbon nanotube array, ultrasonic waves on at least a portion of the carbon nanotube array, mechanical vibration of at least a portion of the carbon nanotube array, and modifying the hydrophobicity of the nanotube array during fabrication.

In yet another aspect, the drug delivery enhancement is executed at a time selected from the group consisting of instantly and according to a timed sequence.

In another aspect of the device of the present invention, the carbon nanotubes are arranged in one or more clusters, such that each cluster effectively functions as a needle.

In another aspect of the device, the substrate comprises a porous material, whereby substances may be transferred to or from the device and the tissue via inherent capillary action of the carbon nanotubes.

In another aspect, the porous substrate material is loaded with a substance to be transferred to the tissue via the carbon nanotubes.

In yet another aspect of the device, the carbon nanotube clusters are patterned in a manner such that they are electrically isolated from one another, and where the device further comprises a sensor for reading electrical potentials of the nanotube clusters.

In another aspect, the inherent electrical conductivity of the carbon nanotubes is modified by treatment of the carbon nanotubes with a pre-coated chemical.

In a further aspect of the present invention, a subset of the carbon nanotube clusters is treated with glucose oxidase, and another subset of the carbon nanotubes is treated with ferric cyanide, whereby conduction through the blood may be achieved and allows for measurement of the blood-glucose level.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

The present invention relates to a nanostructure-enhanced drug delivery and blood monitoring device and, more particularly, to a device with aligned carbon nanotubes protruding from the device surface for facilitating drug or fluid transfer between the device and body tissue. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6.

(1) Introduction

The present invention relates to a nanostructure-enhanced drug delivery and blood monitoring device and, more particularly, to a device with aligned carbon nanotubes protruding from the device surface for facilitating drug or substance transfer between the device and body tissue.

Recent advances in carbon nanotube technology make it possible to create needles or rods with diameters of the order of nanometers (nm) and lengths of the order of millimeters. Carbon nanotubes are beneficial in the present application because the distribution of nerves within the dermal layers is sparse compared to nanoscale needles of size similar to carbon nanotubes. For example, a collection of 200 carbon nanotubes with diameters of 10 nm, in close contact, will occupy less than 2 micrometers in total diameter for the whole collection. U.S. Patent Application Publication No. 2008/0145616 A1 describes a method for selectively anchoring a large number of nanoscale structures. This anchoring method allows control of the depth of anchoring the nanoscale structures into the other material.

(2) Details of the Invention

Carbon nanotubes can be formed in several ways, the simplest being thermal chemical vapor deposition using a catalyst-coated substrate. Typically a few nanometers of iron coated onto silicon, prepared in advance and placed in a tube furnace under flow of carbon-containing feedgas, such as ethylene, and elevated to a proper temperature, e.g., 725 degrees Celsius. Thermal chemical vapor deposition growth of carbon nanotubes (See Literature Reference No. 3) generates vertically aligned carbon nanotubes on the growth substrate, which is typically silicon.

Anchoring an array of carbon nanotubes on a substrate can be done by bringing the array of carbon nanotubes into contact with a layer of uncured polymer material and then undergoing a curing step, as described in previously-cited U.S. Patent Application Publication No. 2008/0145616 A1. In order to anchor carbon nanotubes into a tube-shaped substrate such as a balloon material, a sacrificial release layer may be used around a central rod to keep a cylindrical shape. First, a sacrificial release layer is deposited and formed around the rod and possibly cured, and then the balloon material is deposited around the release layer. The nanotubes are then attached or anchored into the balloon material. Finally, the sacrificial release layer is removed, releasing the balloon with the nanotubes attached or anchoring into it.

Drugs, genes, or other substances may be coated onto carbon nanotubes in another step, either before or after they are attached to the substrate. This is particularly enabled with the drug paclitaxel because it is hydrophobic, and carbon nanotubes are also hydrophobic in their as-grown state. Thus, the paclitaxel molecules will prefer to adhere to the carbon nanotubes until they are placed in close contact with occluding materials in vessels which are usually fatty and hydrophobic in nature. In addition, because the carbon nanotube surface is hydrophobic in nature, any substance residing within the layer of nanotubes will be immune from water and aqueous solutions and mixtures, such as blood, which come in contact with the nanotube surface. Thus, in a desired aspect of the present invention, the tips of the carbon nanotubes are left free of the drug coating, and the drug coating is limited to the side wall of the nanotubes and/or free spaces between nanotubes. This aspect provides a safe surface contact and also avoids premature drug release into non-target tissue or body fluid.

Drug release by the carbon nanotubes into the target tissue can be enhanced by connection with an enhancement device capable of performing a variety of enhancement methods, including but not limited to applying one or more of the following to the carbon nanotubes: direct or indirect heating, for example, by electromagnetic radiation such as radio frequency (RF) waves; electrical current; laser or other optical stimulation; ultrasonic waves; mechanical vibration; and by modifying the hydrophobicity of the nanotube array during fabrication (this can be done, for example, by treatment with oxygen plasma). These enhancement methods can be applied to either a spatially patterned portion of or the complete set of the carbon nanotubes. The methods can also be applied instantaneously or according to a time sequence.

Figure 1:
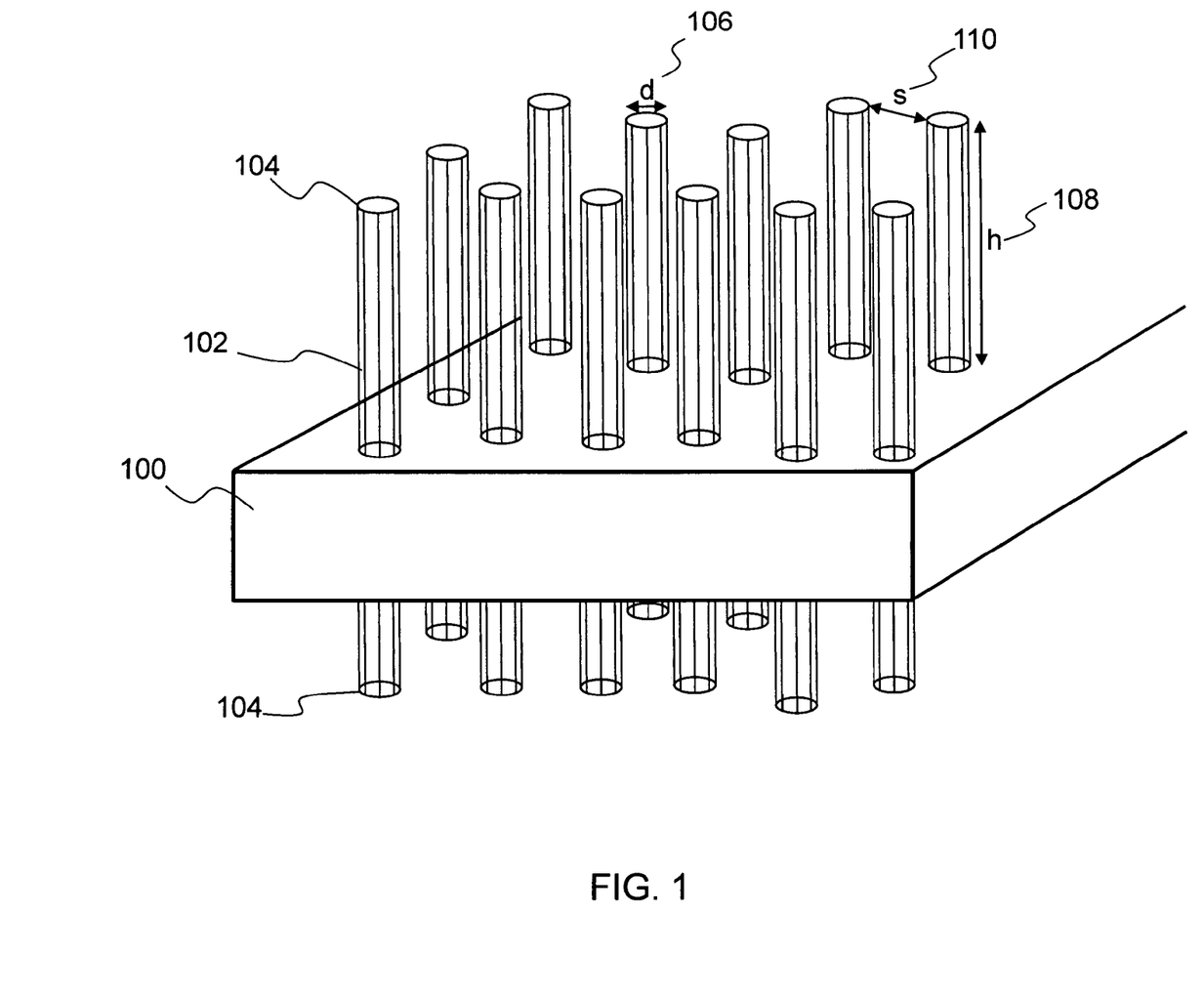
FIG. 1 is a side view of a polymeric anchoring layer with carbon nanotubes protruding therefrom.

FIG. 1 is an illustration showing a generic embodiment of the present invention. The device comprises a substrate layer 100, and a plurality of substantially aligned carbon nanotubes 102. Each carbon nanotube has two ends 104, and the carbon nanotubes 102 are anchored within the substrate 100 with at least one end 104 protruding from the substrate. In the example shown, the carbon nanotubes 102 protrude from the substrate 100 at both ends.

Figure 2A:
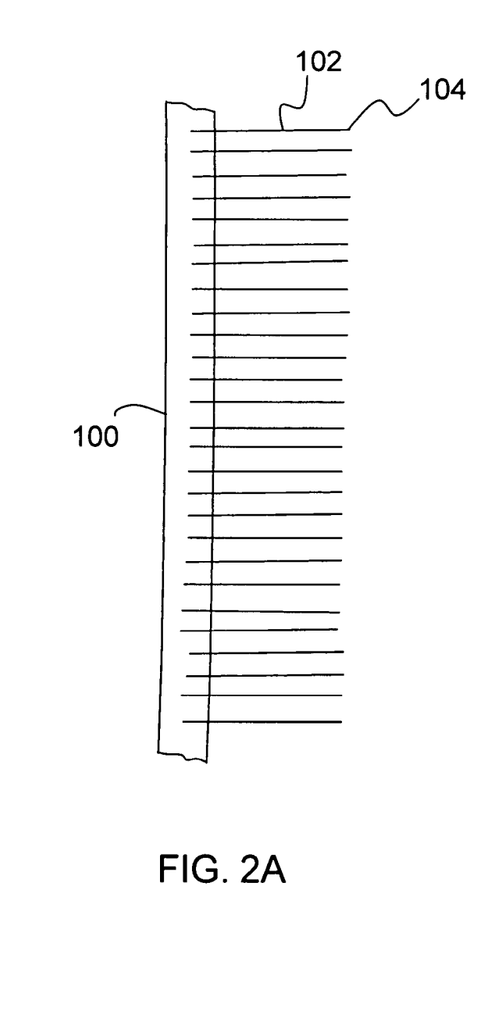
FIG. 2A is a side view of a nano-enhanced device according to the present invention, depicting the carbon nanotubes protruding from the substrate at only one end.
Figure 2B:
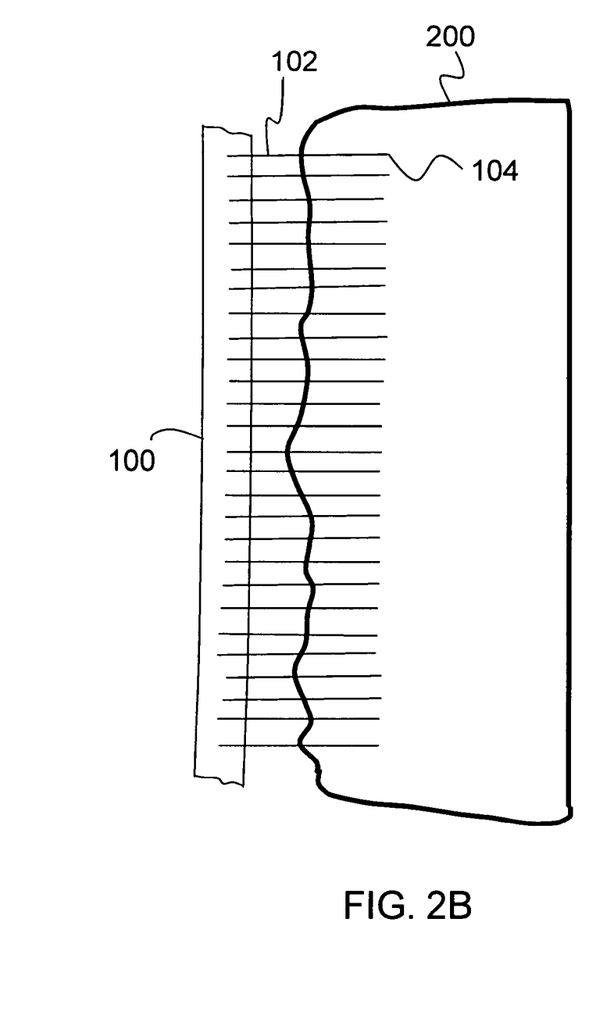
FIG. 2B is a side view of a nano-enhanced device according to the present invention, depicting the device piercing the surface of a tissue.

FIG. 2A illustrates another embodiment of the device, where the aligned carbon nanotubes 102 protrude from the substrate 100 at only one end 104. FIG. 2B shows the end 104 of a carbon nanotube array 102 piercing the surface of a body tissue 200 such as skin, artery wall, colon, etc. It should be noted that the present invention has potential uses outside the medical field as well. The device could feasibly transfer substances to a wide range of targets other than body tissue, and therefore is not limited to that application.

Figure 3A:
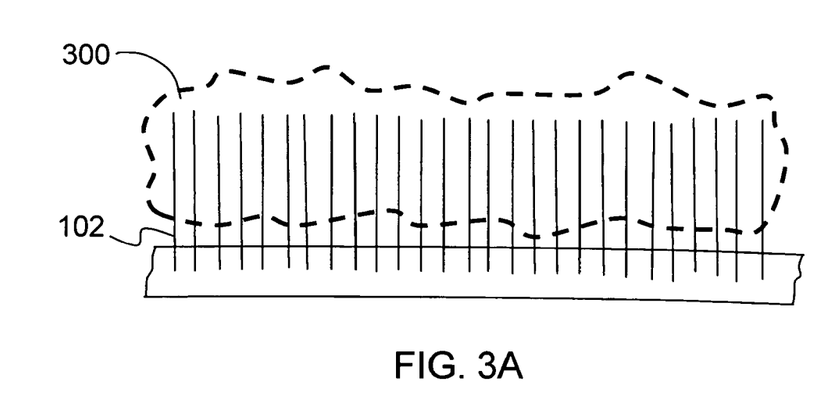
FIG. 3A is a side view of a nano-enhanced device according to the present invention, depicting the carbon nanotubes as coated with a drug or agent.
Figure 3B:
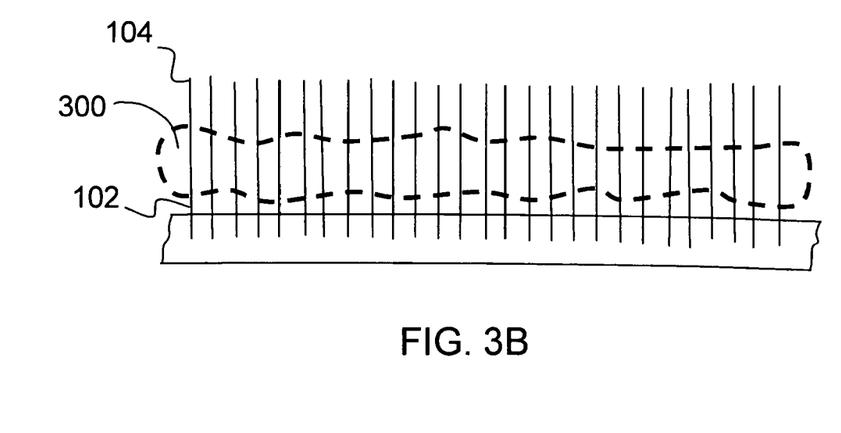
FIG. 3B is a side view of a nano-enhanced device according to the present invention, depicting an interior portion of the carbon nanotube array coated with a drug, but with the nanotube ends being left free of the coated drug.

The carbon nanotubes may be coated with a drug, a gene, or other substance to be transferred to the tissue. FIG. 3A illustrates an embodiment of the device where the carbon nanotubes 102 are coated with a substance 300 to be transferred to body tissue. In an alternate embodiment as shown in FIG. 3B, the ends 104 of the carbon nanotubes are left free of the coated substance 300. The coated substance 300, in this case, would be limited to the side walls of the carbon nanotubes, and/or spaces between the carbon nanotubes.

(3.0) Specific Applications
(3.1) Needle

Figure 4A:
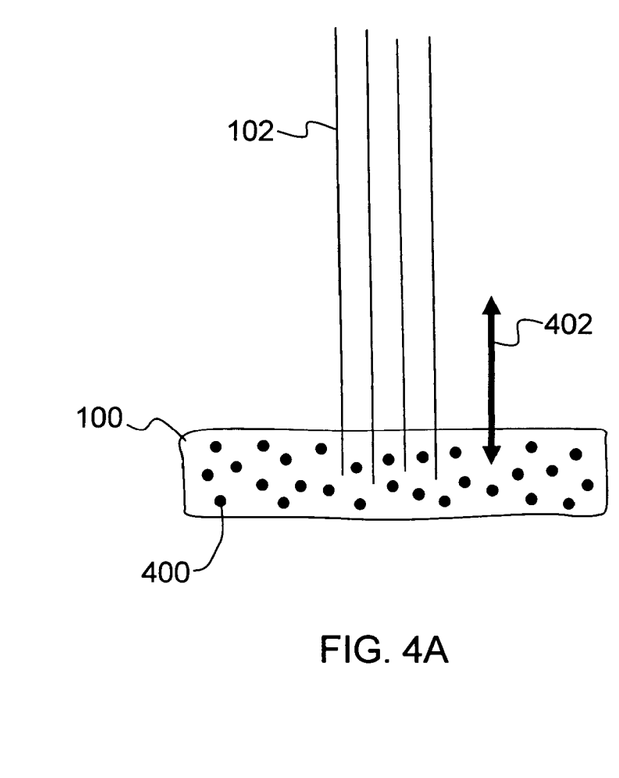
FIG. 4A is a side view of a nano-needle anchored in a porous substrate material in accordance with the present invention.
Figure 4B:
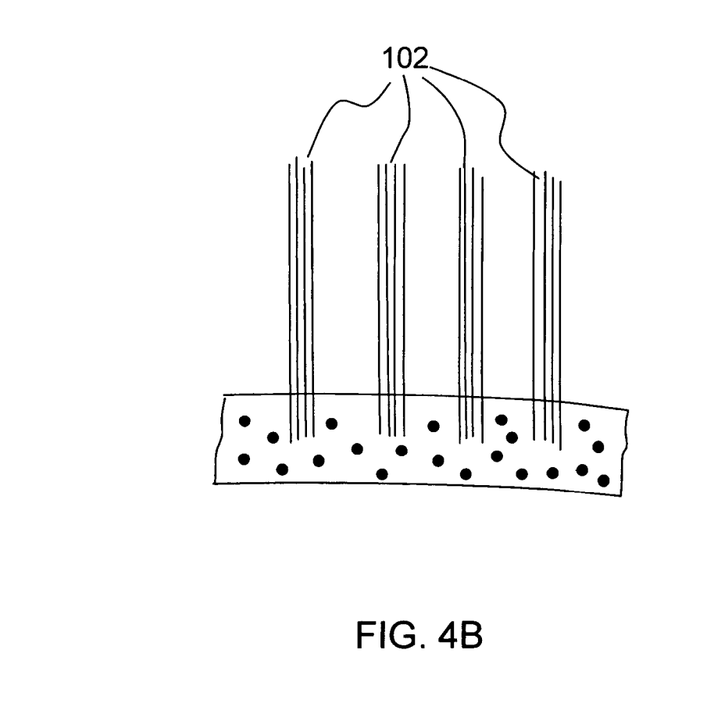
FIG. 4B is a side view of a device having multiple nano-needles protruding therefrom.

One aspect of the present invention is a device that uses a patterned distribution of carbon nanotubes to function as a microscale needle which could easily penetrate dermal layers, reaching microvasculature or interstitial fluids. Such a device could be used as a needle or reverse needle to facilitate transfer of substances to and from the body, respectively. FIG. 4A shows a group of carbon nanotubes 102 anchored into a substrate 100 such that they form a nano-needle. In the embodiment shown, the substrate is porous 400. A two sided arrow 402 shows the possible direction of migration of substances to or from the substrate via the carbon nanotubes 102. When functioning as a needle, blood or interstitial fluids are drawn into the porous substrate 400 through sub-dermal contact of the carbon nanotube based needle with the fluid, similar to the piercing action shown in FIG. 2B. Analysis of the fluid is conducted through some separate means, such as by optical analysis. To function as a reverse needle, the porous substrate 400 is pre-loaded with some agent, for example, medication, which may then be delivered via the carbon nanotube-based needle into the sub-dermal region. FIG. 4B shows a device with multiple needle-like clusters of nanotubes 102.

(3.2) Probe

Figure 5A:
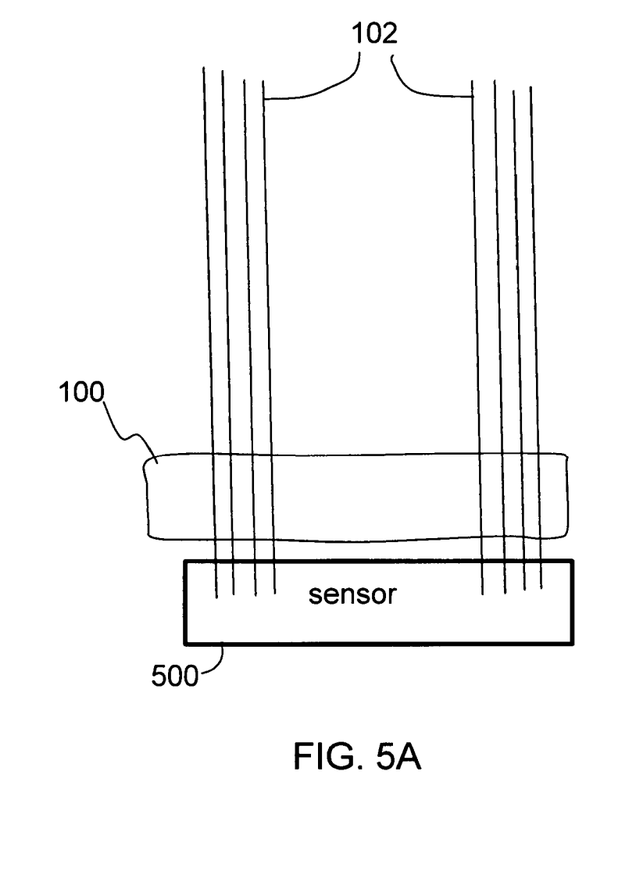
FIG. 5A is a side view of a nano-enhanced device connected with a sensor to form a nano-probe.
Figure 5B:
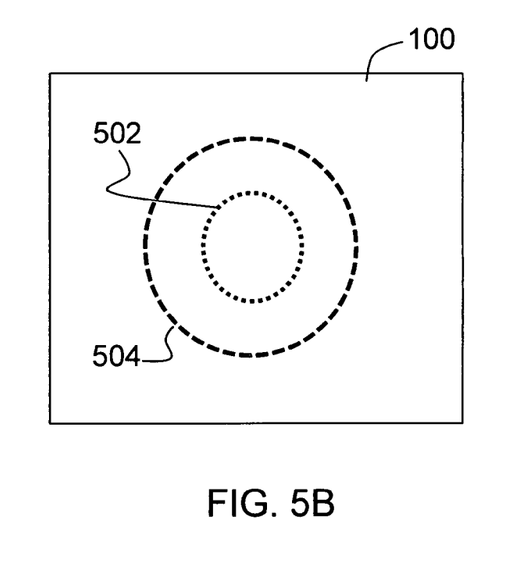
FIG. 5B is a top view of a nano-probe device in accordance with the present invention where the nano-needle clusters are patterned into electrically isolated subsets.

The nano-needle device can be combined with a sensor to function as a probe to monitor blood glucose levels or other blood or body fluid properties, for example pH, sugar level, oxygen content, etc. The device functions based on the inherent electrical conductivity of the carbon nanotubes. FIG. 5A is an illustration of a nano-probe according to the present invention. The probe comprises one or more clusters of carbon nanotubes 102 anchored in a substrate 100 in conjunction with a sensor 500. The sensor may be operatively connected with the carbon nanotubes 102 or with the substrate 100, or both, depending on the desired mode of operation. In FIG. 5A, the sensor 500 is operatively connected with the carbon nanotube 102 clusters. In a desired embodiment as shown in the top-view in FIG. 5B, the nanotube clusters are patterned in such a manner that they are electrically isolated from one another. The pattern shown comprises an inner ring 502 and an outer ring 504 of nanotube clusters. A specific use for the aspect shown in FIG. 5B is measuring blood glucose level. In this application, a subset of the carbon nanotube clusters (for example, the inner ring 502) is treated with glucose oxidase, while another subset of carbon nanotube clusters (for example, the outer ring 504) is treated with ferric cyanide, whereby conduction through the blood may be achieved and allows for measurement of the blood-glucose level. It should be noted that the present invention may employ many patterns of nanotube clusters in addition to the specific embodiment shown in FIG. 5B. Furthermore, the device may also be used as a coated probe, where an agent such as a drug may be pre-coated onto the surface or within the carbon nanotubes as shown in FIGS. 3A and 3B, and thus delivered and released by penetration of the carbon nanotubes into the body tissue.

(3.3) Paintbrush

An assembly of carbon nanotubes as shown in FIG. 4B can also act as a wet paintbrush by virtue of the inherent capillary action of the carbon nanotubes. A similar method is described in U.S. patent application Ser. No. 11/124,523, which is hereby incorporated by reference as though fully set forth herein.

(3.4) Angioplasty Balloon

Another desired embodiment of the present invention is in angioplasty procedures for delivering the drug paclitaxel for the prevention hyperproliferation of tissue cells following the inflation of the balloon to open a section of a blood vessel. However, the present invention should not be construed as limited to use in angioplasty procedures or to delivery of paclitaxel. The present invention could feasibly be used to deliver a large variety of substances to various parts of the body, including, but not limited to, the skin, uterus, bronchial tubes, and various portions of the gastrointestinal tract including colon.

Figure 6A:
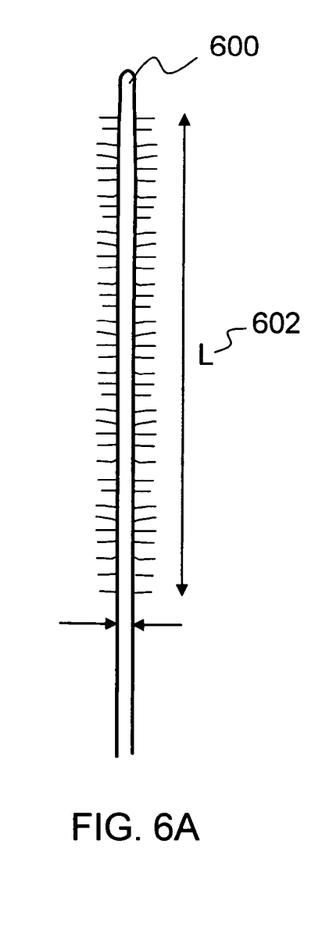
FIG. 6A is an illustration showing a nano-enhanced catheter balloon in accordance with the present invention, where the balloon is in a deflated state.
Figure 6B:
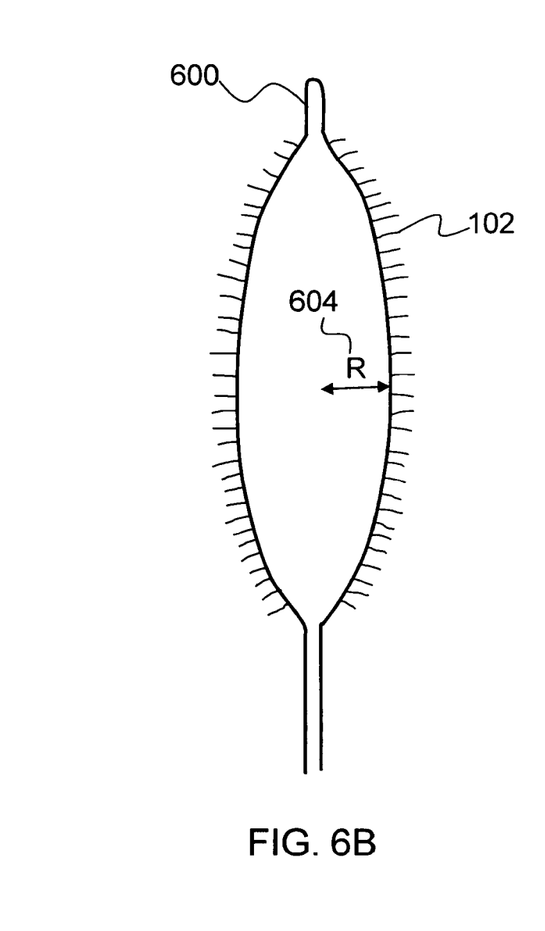
FIG. 6B is an illustration showing a nano-enhanced catheter balloon in accordance with the present invention, where the balloon is in an expanded state.

FIGS. 6A and 6B illustrate a nano-enhanced angioplasty balloon 600 according to the present invention. FIG. 6A shows the angioplasty balloon in deflated form, as it would be inserted into a blood vessel or other body enclosure. Upon inflation, as shown FIG. 6B, the surface carbon nanotubes 102 penetrate the blood vessel surface in the manner shown in FIG. 2B, releasing any drug coated thereon into the target tissue.

The present invention, with relation to use in angioplasty balloons, overcomes the limitations of the related art as described in the Background section above, including long inflation time, reduced drug quantity available due to loss during insertions process, premature and/or undesired delivery to healthy tissue, and a low total amount of drug delivered. Because the possible quantity of drug for delivery is dependent on surface area, the nano-enhanced balloon-catheter will retain more drug quantity though the insertion process and increase the maximum deliverable drug quantity by a factor on the order of 1000 times, similar to the increase in surface area provided by the nanostructures.

The following expression compares the surface area of a nano-enhanced balloon with a standard balloon without nano-enhancement:

$$\frac{A_{nano-balloon}}{A_{standard-balloon}} = \frac{\frac{4\sqrt{3}\pi^2 dhRL}{3s^2}}{2\pi RL} = \frac{2\sqrt{3}\pi dh}{3s^2}$$

where:
d (106 in FIG. 1) is the diameter of an individual carbon nanotube;
h (108 in FIG. 1) is the length of an individual carbon nanotube;
(110 in FIG. 1) is the distance between individual carbon nanotubes;
R (604 in FIG. 6B) is the radius of the balloon; and
L (602 in FIG. 6A) is the length of the balloon, and
using the following assumed typical values:
d=10 nm;
s=100 nm; and
h=500 nm,
the following result is obtained:

$$\frac{A_{nano-balloon}}{A_{standard-balloon}} = 1813.17$$

This result indicates that the surface diffusion enhancement of a catheter balloon as described can easily increase the surface area by a factor of $10^3$.

(3.5) Epidermal Patch

Figure 7A:
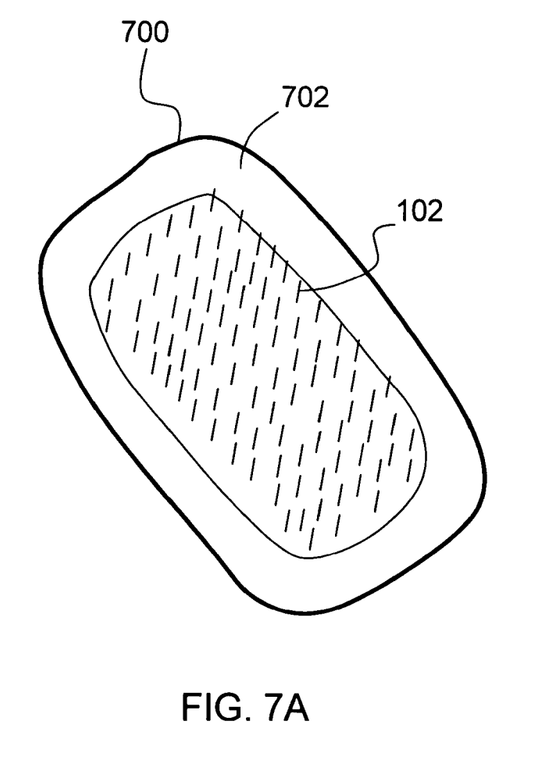
FIG. 7A is a perspective view of a nano-enhanced epidermal patch in accordance with the present invention.
Figure 7B:
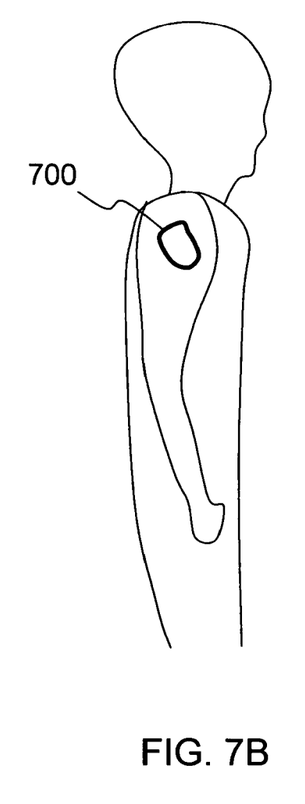
FIG. 7B is an illustration showing a nano-enhanced epidermal patch adhered on the arm of a user.

The nano-enhanced surfaces of the present invention can be incorporated into an epidermal patch to be worn on the skin. FIG. 7A illustrates an example of a nano-enhanced epidermal patch 700. The patch has aligned carbon nanotubes 102 protruding from the surface to be adhered to the skin. A portion of the patch 700, for example the perimeter 702, may be coated with adhesive to facilitate adhesion to the skin. When the patch 700 is applied to the skin as in FIG. 7B, the carbon nanotubes 102 will enter the skin in a manner shown in FIG. 2B and release any drug or agent coated thereon into the skin. The patch may be used in conjunction with any of the previously described embodiments of the present invention.

What is claimed is:

1. A nano-enhanced patch to be worn on a tissue and for substance transfer between the patch and a tissue, comprising:
   a substrate; and
   an array of carbon nanotubes having two ends, the carbon nanotubes being anchored within the substrate with at least one end protruding from the substrate, the carbon nanotubes being grouped in clusters such that each cluster effectively functions as a needle, the protruding carbon nanotube clusters being arranged as a plurality of rings with all of the nanotubes of the clusters being in a ring periphery, whereby the protruding carbon nanotubes allow the transfer of a substance through the substrate and into the tissue.

2. The patch of claim 1, wherein the substrate comprises a porous material, the substance being transferable from the patch to the tissue via inherent capillary action of the carbon nanotubes.

3. The patch of claim 1, wherein the substrate is loaded with the substance to be transferred to the tissue.

4. The patch of claim 1, wherein the carbon nanotubes are coated with the substance to be transferred to the tissue.

* * * * *